(12) United States Patent
Zhang et al.

(10) Patent No.: US 12,310,674 B2
(45) Date of Patent: May 27, 2025

(54) METHOD, APPARATUS, DEVICE AND COMPUTER STORAGE MEDIUM FOR A MEDICAL ASSISTANCE OPERATION

(71) Applicant: NEC Corporation, Tokyo (JP)

(72) Inventors: Ni Zhang, Beijing (CN); Yan Li, Beijing (CN); Bingrong Liu, Beijing (CN); Lin Zhou, Beijing (CN)

(73) Assignee: NEC CORPORATION, Tokyo (JP)

( * ) Notice: Subject to any disclaimer, the term of this patent is extended or adjusted under 35 U.S.C. 154(b) by 161 days.

(21) Appl. No.: 17/790,790

(22) PCT Filed: Jan. 6, 2021

(86) PCT No.: PCT/CN2021/070434
§ 371 (c)(1),
(2) Date: Jul. 5, 2022

(87) PCT Pub. No.: WO2021/139672
PCT Pub. Date: Jul. 15, 2021

(65) Prior Publication Data
US 2022/0370153 A1 Nov. 24, 2022

(30) Foreign Application Priority Data

Jan. 7, 2020 (CN) .......... 202010015105.X

(51) Int. Cl.
*A61B 34/20* (2016.01)
*A61B 1/00* (2006.01)
*A61B 34/10* (2016.01)

(52) U.S. Cl.
CPC ........ *A61B 34/20* (2016.02); *A61B 1/000094* (2022.02); *A61B 34/10* (2016.02); *A61B 2034/101* (2016.02); *A61B 2034/2055* (2016.02)

(58) Field of Classification Search
CPC ... A61B 34/20; A61B 1/000094; A61B 34/10; A61B 2034/101; A61B 2034/2055;
(Continued)

(56) References Cited

U.S. PATENT DOCUMENTS

2007/0055128 A1 3/2007 Glossop
2011/0032347 A1 2/2011 Lacey et al.
(Continued)

FOREIGN PATENT DOCUMENTS

CN 102186404 A 9/2011
CN 104780826 A 7/2015
(Continued)

OTHER PUBLICATIONS

International Search Report of PCT/CN2021/070434 dated Mar. 29, 2021 [PCT/ISA/210].
(Continued)

*Primary Examiner* — Bo Joseph Peng
(74) *Attorney, Agent, or Firm* — Sughrue Mion, PLLC

(57) ABSTRACT

Example implementations of the present disclosure relate to method, apparatus, device and computer-readable storage medium for a medical assistance operation. In a method, input data is obtained from an endoscope; and information related to an operation behavior of the endoscope is determined based on the input data. According to the above method, the information related to the operation behaviors of the endoscope may be provided in real time based on the current spot of the endoscope. Accordingly, a medical assistance operation may be further provided to a doctor in real time during the endoscopic examination. Furthermore, corresponding apparatus, device and computer storage medium are also provided.

7 Claims, 11 Drawing Sheets

(58) Field of Classification Search
CPC .......... A61B 1/0004; A61B 1/000096; A61B 1/0005; A61B 1/00009; A61B 1/00011; A61B 1/00039; A61B 1/00043; A61B 1/00057
See application file for complete search history.

(56) References Cited

U.S. PATENT DOCUMENTS

| | | |
|---|---|---|
| 2012/0062714 A1 | 3/2012 | Liu et al. |
| 2015/0254872 A1 | 9/2015 | de Almeida Barreto et al. |
| 2016/0206228 A1 | 7/2016 | Angulo et al. |
| 2016/0270757 A1* | 9/2016 | Toma .................. A61B 8/5223 |
| 2018/0125591 A1 | 5/2018 | Camarillo et al. |
| 2018/0271603 A1* | 9/2018 | Nir .......................... A61B 34/25 |
| 2019/0201125 A1 | 7/2019 | Shelton, IV et al. |

FOREIGN PATENT DOCUMENTS

| | | |
|---|---|---|
| CN | 106709967 A | 5/2017 |
| CN | 109523522 A | 3/2019 |
| CN | 109846444 A | 6/2019 |
| JP | 2014-131551 A | 7/2014 |
| JP | 2016-063868 A | 4/2016 |
| JP | 2017-108934 A | 6/2017 |
| JP | 2017-144247 A | 8/2017 |
| JP | 2019-097661 A | 6/2019 |
| WO | 2017/175282 A1 | 10/2017 |

OTHER PUBLICATIONS

Notification of Reasons for Refusal issued Oct. 31, 2023 in Japanese Application No. 2022-541812.
Japanese Office Action dated Jun. 4, 2024 in Application No. 2022-541812.
Communication dated Jan. 15, 2025 issued by the State intellectual Property Office of the P.R.China in application No. 202010015105.X.

* cited by examiner

METHOD, APPARATUS, DEVICE AND COMPUTER STORAGE MEDIUM FOR A MEDICAL ASSISTANCE OPERATION

CROSS REFERENCE TO RELATED APPLICATIONS

This application is a National Stage of International Application No. PCT/CN2021/070434 filed Jan. 6, 2021, claiming priority based on Chinese Patent Application No. 202010015105.X filed Jan. 7, 2020.

FIELD

Example implementations of the present disclosure relate to the technical field of medical assistance, and further relate to information processing method, apparatus, device and computer storage medium for medical assistance, and more specifically, relate to method, apparatus, device, and computer storage medium for a medical assistance operation.

BACKGROUND

Medical examinations performed on patients usually involve complicated manual operations. At present, the development of the computer technology has provided more and more support to the medical assistance operations. For example, during the endoscopic examinations, a doctor needs to move the endoscope inside a patient's body to obtain image data at multiple spots inside the body of the patient. There may be differences among operations from various doctors. For example, an experienced doctor may independently complete a full set of endoscopic examinations, while an inexperienced doctor may miss certain predetermined key spots and/or cause discomfort to the patients due to improper operation of the endoscope. Therefore, it is expected to provide an effective technical solution to provide medical assistance so as to guide the operations of the endoscopic examination.

SUMMARY

Example implementations of the present disclosure provide a technical solution for a medical assistance operation.

In a first aspect of the present disclosure, there is provided a method for a medical assistance operation. The method includes: obtaining input data from an endoscope; and determining information related to an operation behavior of the endoscope based on the input data.

In a second aspect of the present disclosure, there is provided an apparatus for a medical assistance operation. The apparatus includes: an input module configured to obtain input data from an endoscope; and an output module configured to determine information related to an operation behavior of the endoscope based on the input data.

In a third aspect of the present disclosure, there is provided a device for a medical assistance operation. The device comprises: at least one processing unit; at least one memory coupled to the at least one processing unit and storing instructions executed by the at least one processing unit, the instructions, when executed by the at least one processing unit, causing the device to perform the method according to the first aspect.

In a fourth aspect of the present disclosure, there is provided a computer-readable storage medium stored thereon with computer-readable program instructions, the computer-readable program instructions being provided for executing the method according to the first aspect.

This Summary is provided to introduce a selection of concepts in a simplified form that are further described below in the Detailed Description. This Summary is not intended to identify key features or essential features of the present disclosure, nor is it intended to be used to limit the scope of the claimed subject matter.

BRIEF DESCRIPTION OF THE DRAWINGS

Through the following more detailed description of the example implementations of the present disclosure with reference to the drawings, the above and other objectives, features and advantages of the present disclosure will become more apparent, wherein in the example implementations of the present disclosure, same reference signs usually indicate the same components.

DETAILED DESCRIPTION OF EMBODIMENTS

Preferred example implementations of the present disclosure will be described in more details with reference to the drawings. Although the drawings show the preferred example implementations of the present disclosure, it should be understood that the present disclosure can be implemented by various manners and should not be interpreted as being limited to the example implementations explained herein. On the contrary, the example implementations are provided for a more thorough and complete understanding of the present disclosure and to fully convey the scope of the present disclosure to those skilled in the art.

As used herein, the term "includes" and its variants are to be read as open-ended terms that mean "includes, but is not limited to." The term "or" is to be read as "and/or" unless the context clearly indicates otherwise. The term "based on" is to be read as "based at least in part on." The terms "an exemplary example implementation" and "one example implementation" are to be read as "at least one exemplary example implementation." The term "a further example implementation" is to be read as "at least one further example implementation". The terms "first", "second" and so on can refer to same or different objects. The following text can comprise other explicit and implicit definitions.

Machine learning technology has been used in many application fields including medical science. It is usually complicated to operate the medical examination devices, especially for endoscopic examination, in which an endoscope needs to be inserted into a patient's body to capture images at various spots of the human body. During the examination procedure, it is ensured that images at a set of key spots are obtained. The endoscope may be operated by a doctor to move along different motion tracks. Some key spots which should have been examined may be missed in case of an improper operation. Therefore, it has become an interest of research about how to more effectively provide a medical assistance operation.

Figure 1:
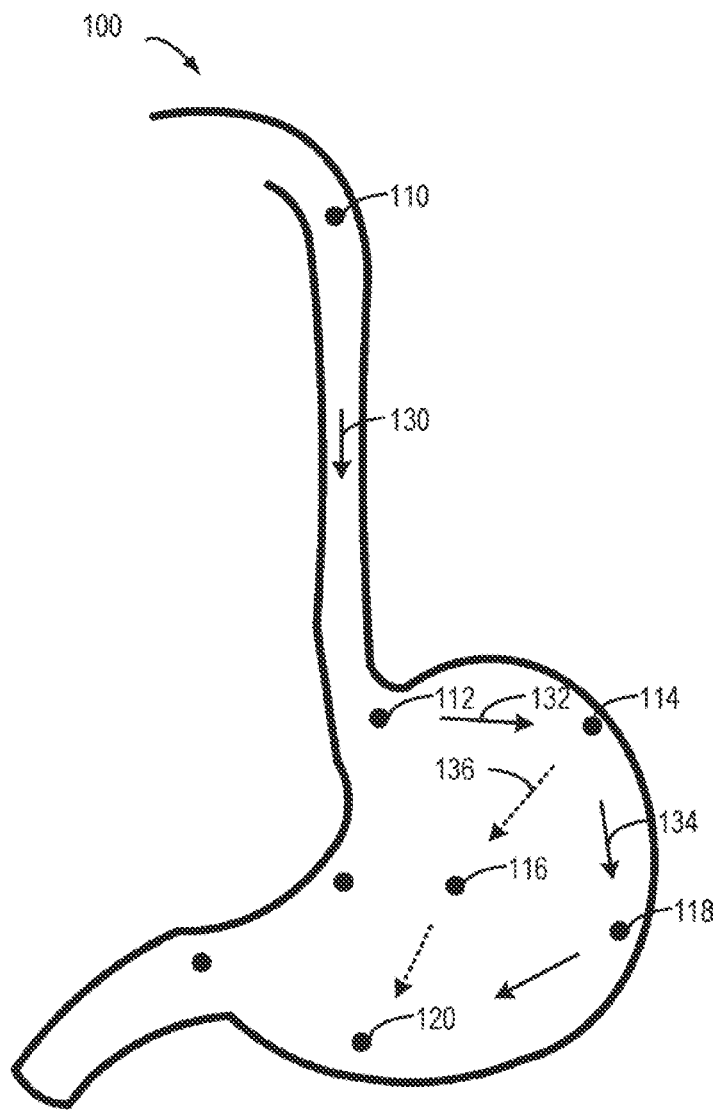
FIG. 1 schematically illustrates a block diagram of a human body environment in which example implementations of the present disclosure may perform the endoscopic examination.

The endoscope may be applied to examine many human body parts and may be divided, for example, into various types, including esophagoscope, gastroscope, duodenoscope and enteroscope etc. depending on a human body part to be examined. In the following description, details of the example implementations of the present disclosure are described by an example of gastroscope. An application environment of the example implementations of the present disclosure is described in the first place with reference to FIG. 1, which schematically illustrates a diagram 100 of a human body environment in which the example implementations of the present disclosure may perform the endoscopic examination. According to the operation specification of the endoscope, the endoscope should reach a set of predetermined key spots during the examination and capture images at these key spots to determine whether an abnormality occurs at the spots. In an embodiment, the spot may be an anatomy spot. As shown in FIG. 1, when the endoscope is inserted into a stomach of a human body, it may pass several key spots 110, 112, 114, 116, 118 and 120 etc.

The endoscope may first go through the pharynx and then reach a key spot 110. As demonstrated by the arrow line 130, the endoscope may go down along esophagus into stomach and finally arrive at a key spot 112. Moreover, the endoscope may reach a key spot 114 as indicated by the arrow line 132. It is to be understood that the endoscope may move along different directions inside the stomach because there is relatively large space inside the human body and a doctor may operate the endoscope in various ways. For example, when the endoscope reaches the key spot 114, it may either arrive at a key spot 118 along a direction denoted by the arrow line 134, or it may arrive at a key spot 116 along a direction represented by the dashed arrow line 136.

Although a set of key spots have been defined in the operation specification, the doctor could only rely on his/her personal experience to adjust the motion track of the endoscope. It is also possible that the motion track only covers a part of the key spots.

Figure 2:
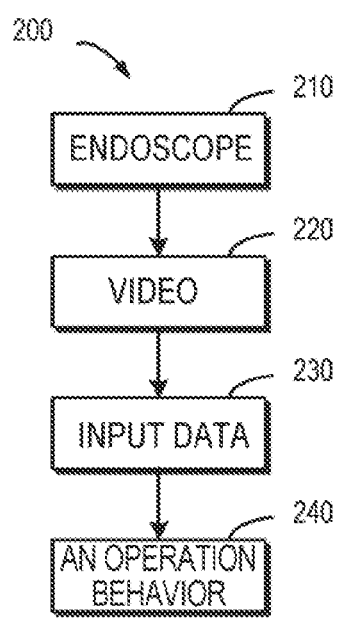
FIG. 2 schematically illustrates a block diagram of a medical assistance operation in accordance with example implementations of the present disclosure.

To at least partially solve the above deficiencies in the endoscopic examination, there is provided a technical solution for a medical assistance operation in accordance with example implementations of the present disclosure. An outline of the technical solution is first described with reference to FIG. 2, which schematically illustrates a block diagram 200 of a medical assistance operation in accordance with example implementations of the present disclosure. According to FIG. 2, as the endoscope 210 being inserted into a human body and moves inside the human body, the endoscope 210 may capture a video 220, which may be observed in real time by the doctor.

It is to be understood that input data 230 (for example, including image data sequence) may be obtained based on the video 220. For example, the input data 230 may include one or more video clips, wherein one video clip may include images captured when the endoscope 210 passes the pharynx of the human body and another video clip may include images captured when the endoscope 210 goes through the esophagus of the human body. It is to be appreciated that the format of the input data 230 is not limited in the context of the present disclosure. For example, the input data 230 may include video data, a set of image sequences in the video which is sorted according to time sequence, or image data with time information. In accordance with example implementations of the present disclosure, the input data may be saved in an original video file format or in a self-defined intermediate format.

It will be understood that the input data may be identified using a unique identifier. For example, the ID of the doctor and the time when the examination is performed may serve as the identifier; the ID of the endoscopy equipment and the time when the examination is performed may serve as the identifier; the ID of the patient and the time when the examination is performed may serve as the identifier; alternatively, the above options may be combined to provide a unique identifier. Afterwards, information related to an operation behavior 240 of the endoscope 210 may be determined based on the input data 230.

In this way, effective medical assistance may be provided to the doctor and further guide the operation of the doctor (especially those inexperienced), to avoid missing key spot(s). Moreover, in accordance with example implementations of the present disclosure, the doctor may be guided to traverse all key spots as quickly as possible. This can increase the efficiency of endoscopic examinations, shorten the time period that the endoscope 210 stays inside the body of a patient, and further reduce uncomfortable experience of the patient.

Specifically, a medical assistance operation may be provided in real time while the doctor is performing the endoscopic examination. The information related to an operation behavior of the endoscope may be provided in real time based on the current spot of the endoscope. For example, at least one of the following may be provided in real time: a key spot where the endoscope is currently located, an image related to a key spot, the track which the endoscope has already moved, next destination spot of the endoscope, and statistical information of the endoscopic operations etc. For example, the above information may be displayed on a dedicated display apparatus. Alternatively and/or additionally, the above information may also be displayed on a display apparatus of the endoscopy equipment.

Figure 3:
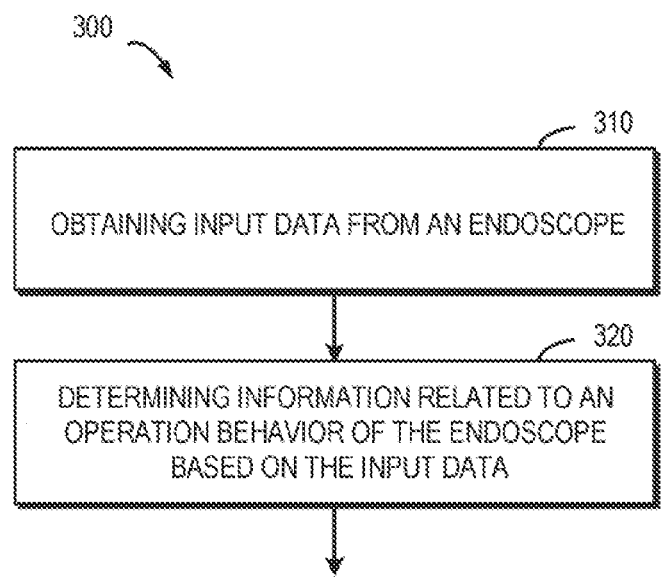
FIG. 3 schematically illustrates a flow chart of a method for a medical assistance operation in accordance with example implementations of the present disclosure.

In the description below, more details of a medical assistance operation are to be described with reference to FIG. 3, which schematically illustrates a flow chart of an operation method 300 for a medical assistance operation in accordance with example implementations of the present disclosure. At block 310, input data 230 may be obtained from the endoscope 210. It is to be understood that input data at different spots may be obtained while the endoscope 210 is moving inside the human body.

The input data 230 may be used to determine information or data required for endoscopic examination. Furthermore, the input data 230 may also be provided for determining information or data related to an operation behavior of the endoscope. As an example, input data 230 may include image data captured at various spots during the motion of the endoscope 210. It is to be understood that the image data here may be the originally captured data or the processed (e.g., denoised or brightness-tuned) data. Depending on a frequency for capturing an image by an image capture apparatus of the endoscope 210, the image data, for example, may include images at 30 frames per second (or other frame rate). It is to be understood that the format of the input data 230 is not limited in the context of the present disclosure.

The input data 230 herein may include at least one of the following: video data, a set of image sequences sorted in accordance with time sequence, and image data with time information. For example, video data may include video streaming format and may support multiple standards of video formats. For another example, an image sequence also may include a series of individual images. At this time, the volume of the input data 230 obtained may gradually increase as the endoscopic examination proceeds. For example, when the endoscope reaches pharynx, an image sequence of the pharynx may be obtained; when the endoscope arrives at esophagus, an image sequence of the esophagus may be further obtained.

In addition, identification corresponding to the input data 230 may be further obtained or determined, to identify the input data 230. Different identifications may distinguish the one of the followings or any combination thereof: different patients, different examination time, different examination spots, and different examination operators.

In accordance with example implementations of the present disclosure, information related to an operation behavior of the endoscope is determined based on the input data at block 320. Information here may include content from various aspects, such as current spot of the endoscope, image data captured at the current spot, motion track of the endoscope, next destination spot of the endoscope, statistical information of the input data, and statistical information of the operation behaviors, etc. In the following description, more details will be depicted with reference to FIGS. 4A and 4B.

As an example, information related to an operation behavior of the endoscope may be determined according to a time-sequence relationship of the input data 230. In addition, in accordance with example implementations of the present disclosure, information related to an operation behavior 240 from various aspects may be determined using the input data 230 based on the machine learning technology. For example, the current spot and the motion track of the endoscope 210 may be determined. It is also determined whether the motion track arrives at the key spot to be examined as expected.

Figure 4A:
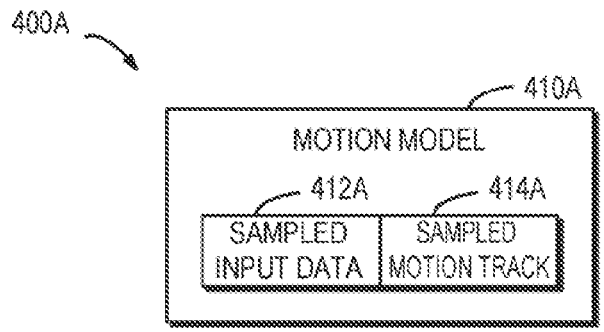
FIG. 4A schematically illustrates a block diagram of the motion model in accordance with example implementations of the present disclosure.

Moreover, the next destination spot to be reached may be determined. Specifically, a motion model 410A may be obtained based on machine learning technology by using sampled data collected during historical operations. FIG. 4A schematically illustrates a block diagram 400A of a motion model 410A in accordance with example implementations of the present disclosure. The motion model 410A may include an association between sampled input data 412A and sampled motion track 414A. The sampled input data 412A here may be captured at various sample spots during the endoscopic examination, and the sampled motion track 414A may include a motion track of the endoscope for capturing the sampled input data 412A.

It is to be appreciated that the sampled input data 412A and the sampled motion track 414A herein may be the sampled training data for training the motion model 410. In accordance with example implementations of the present disclosure, the sampled input data 412A and the corresponding sampled motion track 414A may be used to perform an iteration of training. In the context of the present disclosure, the sampled training data from one or more endoscopic examinations may be used separately for executing one or more iterations of training.

It is to be understood that the motion model 410A as schematically illustrated above is only an example. In accordance with example implementations of the present disclosure, other models may also be provided. For example, another model may include an association between sampled input data captured at multiple sampled spots during the endoscopic examination and the key spots corresponding to the multiple spots where the sampled input data is captured. Respective image data in the input data 230 may be separately mapped to corresponding key spots by employing the model. Therefore, the key spots by which the endoscope goes may be determined based on the model and the input data. Furthermore, the motion track of the endoscope may be determined according to the capture time of the image data and the above key spots.

As an example, the training may be executed based on Recurrent Neural Network (RNN), Long Short Term Memory (LSTM) among other techniques to obtain the motion model 410A. In accordance with example implementations of the present disclosure, the motion model 410A may be obtained by means of the above training method based on the sampled input data captured during the historical examinations and the corresponding sampled motion track. In accordance with example implementations of the present disclosure, the endoscopic examination operations may be executed by the doctor and the captured data may act as samples to train the above model.

For example, an experienced doctor may operate the endoscope to move according to the operation specification of the endoscope. At this time, the sampled motion track of the endoscope may cover all key spots in need of medical examinations. In terms of the input data obtained during one round of endoscopic examination, an association between each sampled image in the input data and the spot of the sampled image in the motion track may be identified by labels.

For example, an experienced doctor may carry out several endoscopic examinations, to obtain sampled image sequences associated with multiple sampled motion tracks. For another example, several experienced doctors may separately perform one or more rounds of endoscopic examinations, to obtain more abundant training data. While adequate training data have been obtained, the motion model 410A may be trained based on the sampled image sequences and the sampled motion tracks. Here, the operation specification of the endoscope defines all the key spots to be examined and the experienced doctors may ensure that the examination performed can meet the requirements in the specification to a maximum extent. When the training is carried out using the training data obtained in the above way, it is ensured that the obtained motion model 410A can accurately reflect the association between images and motion tracks. In addition, the motion model 410A also may be obtained by computer simulation.

For the purpose of description, the example implementations of the present disclosure are described below by an example of an image sequence as the input data 210. When the input data 210 is stored in other formats, the processing of the input data is also similar. For example, when the input data 210 is in a video file format, an image sequence in the video may be obtained and processed accordingly.

In the following description, a process for obtaining the motion model 410A is to be described with reference to FIG. 4B, which schematically illustrates a block diagram 400B of a process for obtaining the motion model 410A in accordance with example implementations of the present disclosure. The training may be executed based on the sampled image sequences and sampled motion tracks captured during the historical examinations. Multiple sampled image sequences may be divided into several groups and each group includes N images, wherein N is an integer and great than 3. Then, a group of multiple frames of sampled images 410B (e.g., consecutive N frames of images starting from T-N-th frame) is input to a neural network layer 412B; a group of multiple frames of sampled images 420B (e.g., consecutive N frames of image starting from T-th frame) is input to a neural network layer 422B; a group of multiple frames of sampled images 430B (e.g., consecutive N frames of image starting from T+N-th frame) is input to a neural network layer 432B. In this way, the association between the image sequences and the motion tracks may be obtained.

Figure 4B:
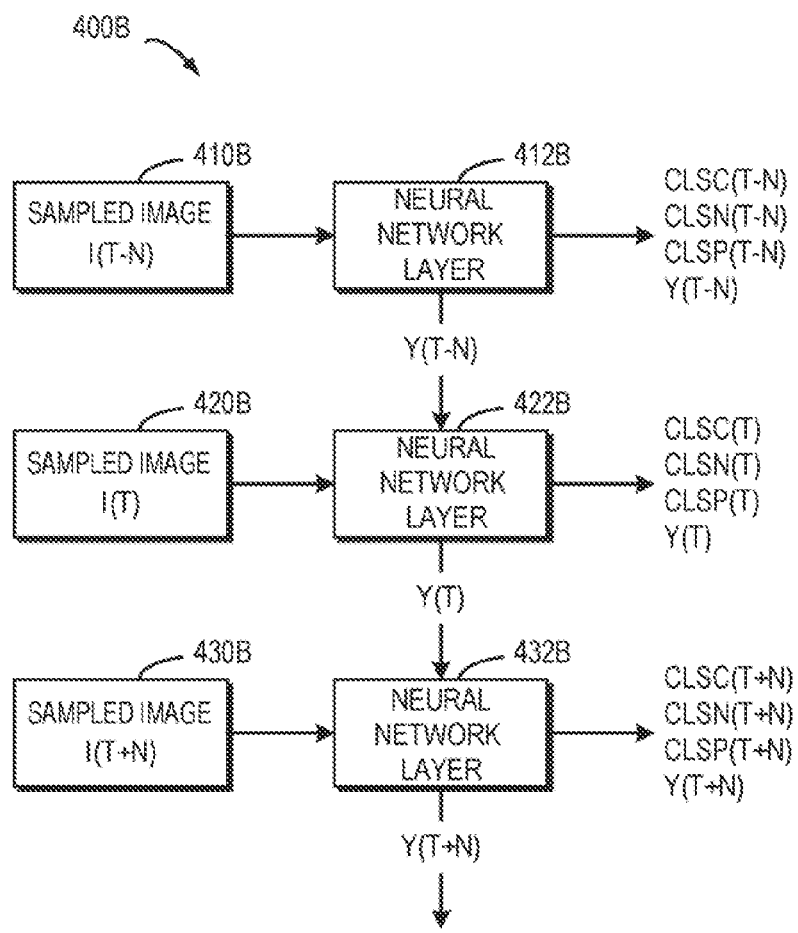
FIG. 4B schematically illustrates a block diagram of a process for obtaining the motion model in accordance with example implementations of the present disclosure.

It is to be appreciated that the above description only schematically illustrates one implementation for obtaining the motion model 410A with reference to FIG. 4B. In accordance with example implementations of the present disclosure, the motion model 410A may be obtained by other machine learning techniques currently known and/or to be developed in the future.

The motion track of the endoscope 210 may be determined based on the motion model 410A and the input data. In accordance with example implementations of the present disclosure, the motion track of the endoscope 210 includes a set of key spots during the motion of the endoscope 210. The set of key spots here includes at least a part of a set of predetermined spots of the human body that the endoscope 210 examines during the endoscopic examination, and multiple spots which the endoscope goes by during its motion may be located within a predetermined range around the key spots.

It is to be appreciated, the set of key spots here may be spots defined by the specification of the endoscopic examination, e.g., including pharynx, esophagus, cardia and pylorus, etc. Assuming that the endoscope passes through the pharynx and has captured 3 images at several spots (e.g., 0.5 cm from the pharynx before reaching the pharynx, the pharynx, and 0.5 cm from the pharynx after leaving the pharynx) near the pharynx during the motion, it may be determined at this moment that the motion track includes the key spot of "pharynx". As the endoscope 210 goes deeper, the motion track may include more key spots, such as pharynx, esophagus and the like. The above spots also may be further divided into more sub-spots. The esophagus, for example, may further include upper esophagus, middle esophagus, and lower esophagus among other spots. In other words, the motion track here may include one or more key spots that the endoscope 210 passes.

In accordance with example implementations of the present disclosure, the captured input data 230 may be input into the motion model 410A in a way similar to the process of acquisition of the motion model 410A. For example, the input data 230 may be divided into multiple groups (each group including N frames of images). The divided multiple groups are successively input into the motion model 410A. By now, at a given layer of the motion model 410A, features (as hidden variables) corresponding to the current N frames of the images may be continuously output and iteratively input to a position of the next layer. The motion model 410A may output the motion track of the endoscope based on the input data that is input to the motion model 410A.

In accordance with example implementations of the present disclosure, the input data may be respectively mapped to a set of key spots by using the motion model 410A.

Continuing to refer to FIG. 4B, as shown by the right side of FIG. 4B, CLSC(T) represents a prediction for key spots to which the consecutive N frames of images starting from the T-th frame belong; CLSN(T) represents a prediction for the key spots to which the subsequent N frames of images belong; CLSP(T) represents a prediction for the key spots to which the previous N frames of images belong; and Y(T) is a prediction for the motion track to which the current image sequences belong. The prediction for the motion track here may include a plurality of key spots. For example, the prediction for a motion track may include: the key spot 110→the key spot 112→the key spot 114; the prediction of the motion track may include: the key spot 110→the key spot 112→the key spot 116. Depending on the current input N frames of images, the prediction of the motion track may include various key spots. The next destination spot may be determined based on the prediction of the motion track. Moreover, the information associated with other frames may be determined in a similar way.

Figure 5:
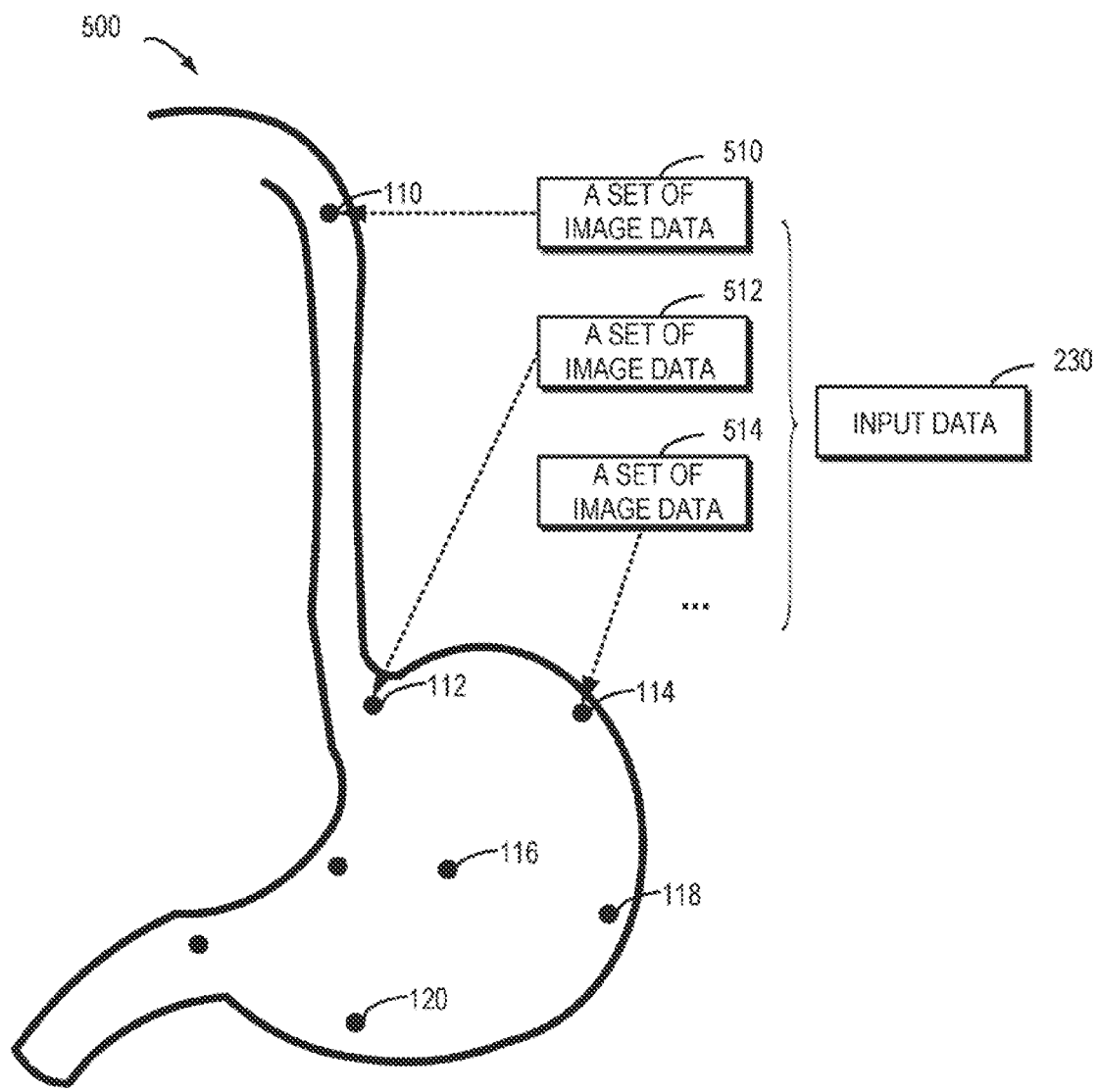
FIG. 5 schematically illustrates a block diagram of a process for mapping a set of image sequences in the image sequences to a set of key spots in accordance with example implementations of the present disclosure.

FIG. 5 schematically illustrates a block diagram 500 of a process for mapping the input data to a set of key spots in accordance with example implementations of the present disclosure. As shown in FIG. 5, the input data 210 will include more and more images as the endoscope 210 stays and moves inside the human body for a long time. FIG. 5 only schematically illustrates the situations at an initial stage of the endoscopic examination. At this time, the endoscope 210 has captured massive images near the key spots 110, 112 and 114.

These images may be mapped to corresponding key spots by employing the above described method. For example, a set of image data 510 in an image sequence may be mapped to the key spot 110, to indicate that the set of image data 510 includes images captured near the key spot 110. Similarly, a set of image data 512 in an image sequence may be mapped to the key spot 112, and a set of image data 514 in an image sequence may be mapped to the key spot 114.

By means of the example implementations of the present disclosure, a spot at which the respective image data is captured may be determined based on the input data 230 captured during the motion of the endoscope 210. In comparison to a technical solution in which a determination is made solely depending on the personal experience of a doctor, the above technical solution can determine a key spot associated with the image data more accurately, to facilitate selecting these images to be stored in the subsequent stages.

In accordance with example implementations of the present disclosure, the motion track may be determined based on the sequence of time when the image sequences associated with the key spots are captured. Continuing to refer to FIG. 5, it has been determined that a set of image data 510 is associated with the key spot 110, a set of image data 512 is associated with the key spot 112, and a set of image data 514 is associated with the key spot 114. Assuming that the respective images that are sorted according to the time sequence when they are captured as follows: the set of image data 510, the set of image data 512 and the set of image data 514. It may be determined at this moment that the motion track 1 includes the key spot 110→the key spot 112→the key spot 114.

It is to be appreciated that the motion track includes the key spots sorted by time sequence. As such, if the sequence of the key spots in a set of key spots varies, a different motion track is indicated. For example, a motion track 2 may include: the key spot 110→the key spot 114→the key spot 112. Accordingly, the motion track 2 is different from the motion track 1.

In addition, the motion track also may be the actual motion track of the endoscope moving inside the parts of the human body, which is determined based on the input data. The actual motion track may include both key spots and non-key spots to reflect the operation behaviors of the endoscope in real time, so as to analyze and guide the endoscopic examination operations more efficiently.

In accordance with example implementations of the present disclosure, the motion track of the endoscope 210 is recorded in a more accurate way based on the sequence of time when the respective image data is captured. Moreover, the determined motion track also may be used for subsequent processing. For example, a key spot supposed to be reached may be determined based on a key spot at which the endoscope 210 has already arrived.

In general, during the endoscopic examination, the doctor manipulates the endoscope to arrive at the expected key spots and stores images for subsequent diagnosis. As the image sequences captured during the examination takes up a large amount of storage space, the doctor usually selects a suitable angle based on his/her personal experiences to capture and store the images only after the endoscope reaches the vicinity of a key spot. For example, a foot pedal may be disposed at the endoscopic examination equipment and the doctor may store the images by stepping on the foot pedal. However, in such a case, it is also possible for the doctor to leave out some key spots and/or stored images which are of poor quality and may not be used for diagnosis.

In accordance with example implementations of the present disclosure, a set of determined images may also be analyzed, such that the doctor may select an image which best reflects the state of the human body at a given key spot. In the following text, more details related to selecting and storing images are to be described with reference to FIG. 6, which schematically illustrates a block diagram 600 of a process of selecting images associated with the key spots for storage in accordance with example implementations of the present disclosure. To be specific, for a given key spot within a set of key spots, a set of given images which are mapped to the given key spot in the input data may be determined.

Figure 6:
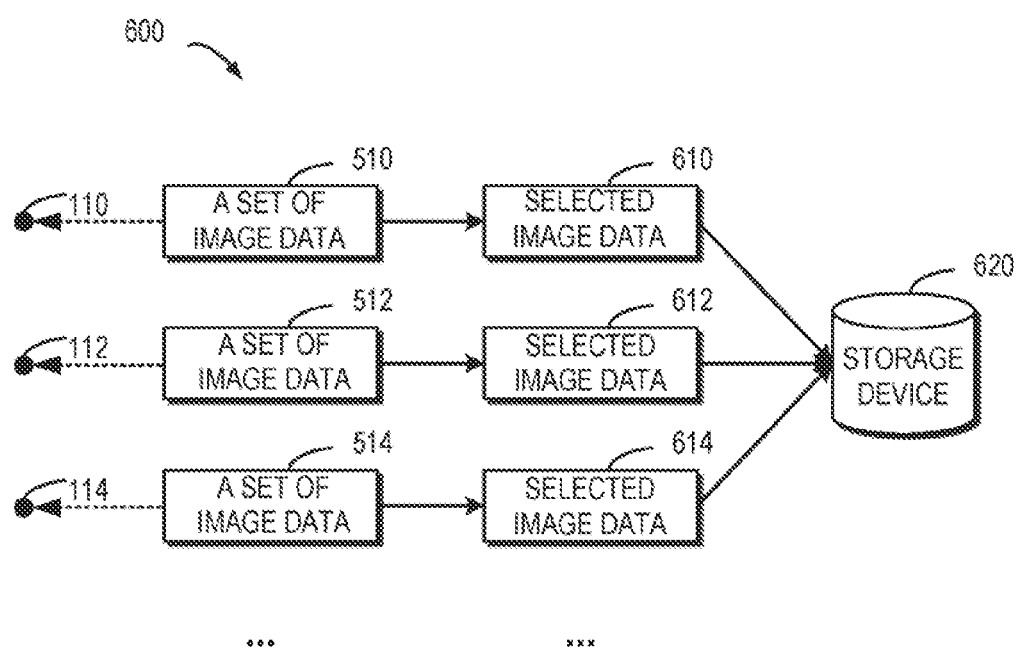
FIG. 6 schematically illustrates a block diagram of a process of selecting images associated with the key spots for storage in accordance with example implementations of the present disclosure.

As shown in FIG. 6, image quality assessment of a set of given images may be determined respectively based on the image quality of a set of given image data. Afterwards, images to be stored may be selected based on the determined image quality assessment. In FIG. 6, a set of image data 510 related to the key spot 110 have been determined. At this moment, the image quality assessment may be determined for the set of image data 510. Subsequently, selected image data 610 may be obtained from the set of image data 510 based on the image quality assessment and the selected image data 610 is stored into a storage device 620. Likewise, selected image data 612 may be obtained from a set of image data 512 and stored into a storage device 620; and selected image data 614 may be obtained from a set of image data 514 and stored into a storage device 620. Next, related information of the stored images may be displayed to the doctor, e.g., the number of stored images and the associated key spots, etc.

It will be appreciated that the image quality herein may include meanings in various aspects, e.g., images may satisfactorily reflect a key spot to be examined. For example, image quality may include one or more of the following: clarity of human mucosa in the images captured by the endoscope, whether the mucosa is contaminated or not, whether the mucosa is covered by secreta or not, and capturing angle of the endoscope etc. If the human mucosa is clearly visible, uncontaminated or not covered by secreta, it may be determined that the image is of a high quality; otherwise, the image may be determined to have a low quality.

It will be understood that the image quality may be determined by various methods. For example, image resolution may be determined based on the image processing methods, such that the image quality assessment may be obtained. For another example, a quality prediction model may be built using pre-labeled sampled data according to a machine learning method. In accordance with example implementations of the present disclosure, the image quality assessment also may be obtained using other image processing techniques currently known and/or to be developed in the future.

In accordance with example implementations of the present disclosure, one or more images having the best image quality may be selected from massive images obtained at the given key spots. Compared to the technical solution in which the image is manually selected and stored based on the personal experiences of the doctor, the technical solution in accordance with example implementations of the present disclosure can significantly improve the efficiency for image selection, reduce the time spent by the doctor for selecting and storing the images, and further improve the efficiency of the endoscopic examination. For another aspect, the operations of mapping, selection and storage of the images are carried out automatically. This may avoid missing of key spots caused by doctor's mistakes. In addition, the present disclosure may facilitate selecting an image of a better quality according to the obtained time-sequence relationship of the input data (e.g., associations between image sequences or images at key spots).

In accordance with example implementations of the present disclosure, assessment of the motion track may be determined based on the motion track of the endoscope 210 and a predetermined motion track of the endoscopic examination. The predetermined motion track here may be a sequence of a series of key spots defined by the specification for operating the endoscope. For example, the predetermined motion track may include pharynx→esophagus→cardia→pylorus, etc. It is expected that the doctor may operate the endoscope to move according to the predetermined motion track. Therefore, the assessment may be determined according to the consistency between the actual motion track and the predetermined motion track of the endoscope 210.

In accordance with example implementations of the present disclosure, variety of types of assessment may be included. For example, the assessment may be represented by a score within a certain range (e.g., real numbers between 0 and 1), or may be represented as a grade (such as high, medium, low), or may be represented by text description, or by images or other ways.

Figure 7A:
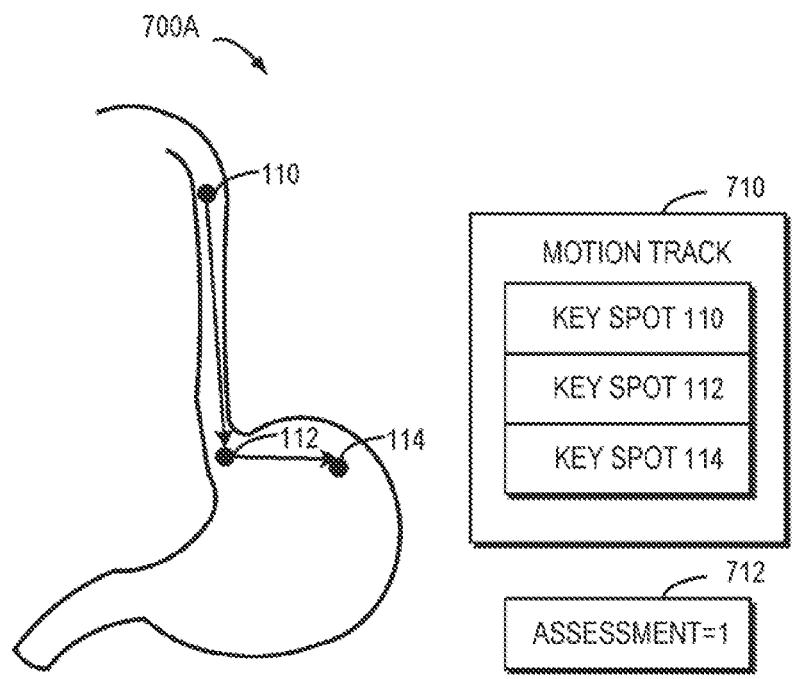
FIG. 7A schematically illustrates a block diagram of data structure of the motion track in accordance with example implementations of the present disclosure.

In the following description, more details related to determining the assessment of the motion track will be described with reference to FIG. 7A, which schematically illustrates a block diagram 700A of data structure of the motion track in accordance with example implementations of the present disclosure. In FIG. 7A, the motion track 710 of the endoscope 210 includes three key spots, i.e., key spots 110, 112, and 114. Currently, the endoscope 210 is at the key spot 114 and the assessment of the motion track 710 may be determined by comparing the motion track 710 with the predetermined motion track of the endoscopic examination. Moreover, relevant assessment may be displayed to the doctor.

It is to be appreciated that the assessment may be determined via different ways. A numerical range may be assigned for the assessment. For example, the assessment may be indicated within a range from 0 to 1. Assuming that the predetermined motion track includes: key spot 110→key spot 112→key spot 114→key spot 118 . . . , and the motion track 710 currently contains key spot 110→key spot 112→key spot 114, it is determined that the motion track 710 is a complete match for the beginning part of the predetermined motion track. Therefore, a relatively high assessment 712 may be given to the motion track 710. For example, the assessment 712 may be set to the highest score of 1. For another example, assuming that the motion track deviates from the predetermined motion track, then the value of the assessment may decrease. For example, the assessment may be set to be 0.8.

It is to be appreciated that the principle for determining an assessment is only schematically described above. In accordance with example implementations of the present disclosure, an assessment prediction model may be built by using pre-labeled sampled data based on the machine learning method. In accordance with example implementations of the present disclosure, the motion track also may be assessed using other prediction techniques that are currently known and/or to be developed in the future.

Figure 7B:
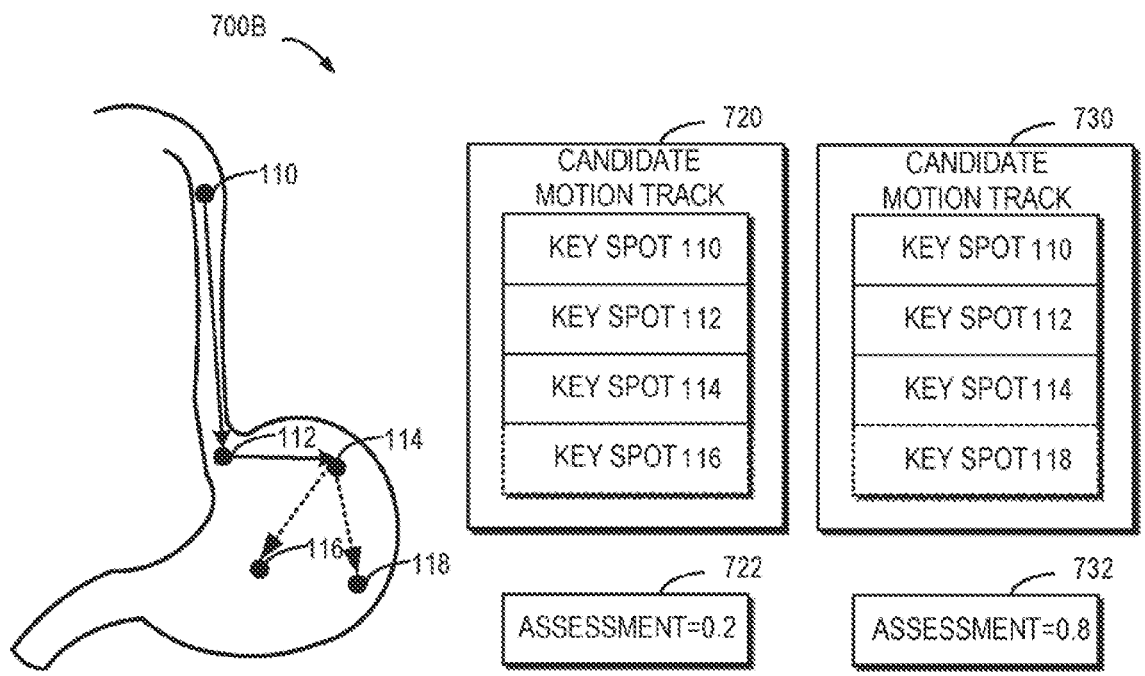
FIG. 7B schematically illustrates a block diagram of a process for providing a next destination spot in accordance with example implementations of the present disclosure.

In the following text, more details related to determining the next destination spot are to be described with reference to FIG. 7B. In accordance with example implementations of the present disclosure, a set of candidate spots may be determined based on one or more key spots near the last key spot in the motion track. FIG. 7B schematically illustrates a block diagram 700B of a process for providing the next destination spot in accordance with example implementations of the present disclosure. As shown in FIG. 7B, a set of candidate spots of the endoscope 210 for the next time point may be determined in the first place. Continuing with the above example, the endoscope 210 is currently located at the key spot 114, and the key spots 116 and 118 are near the critical spot 114. By now, a set of candidate spots may include the key spots 116 and 118. Then, assessment for the respective candidate spots in the set of candidate spots may be determined and the next destination spot is selected from the set of candidate spots based on the determined assessment.

To be specific, for a given candidate spot in the set of candidate spots, a candidate motion track of the endoscope 210 may be generated based on the motion track and the candidate spots. According to FIG. 7B, a candidate motion track 720 may be generated based on the motion track 710 and the key spot 116; and a candidate motion track 730 may be generated based on the motion track 710 and the key spot 118. Afterwards, assessments 722 and 732 for the candidate motion tracks 720 and 730 may be determined based on the candidate motion tracks 720 and 730 and the predetermined motion track of the endoscopic examination, respectively. As shown in FIG. 7B, the value of the assessment 732 is higher than the value of the assessment 722, so a higher assessment may be assigned to the key spot 118, and the key spot 118 may serve as the next destination spot.

Through the example implementations of the present disclosure, key spots that best match the predetermined motion track of the endoscope 210 may be preferably recommended to the doctor as the next destination spot towards which the endoscope 210 moves. In this way, the motion operation of the doctor may also be guided, so as to reduce the potential risks of missing the key spots and improve the efficiency of the endoscopic examination.

Furthermore, the motion of the endoscope inside the human body may cause discomfort to the patients. As the examination efficiency improves, the time period of the endoscopic examination reduces, which decreases the discomfort suffered by the patient.

It is to be appreciated that although a specific example for providing the next destination spot has been described in the above description with reference to the drawings, a subsequent recommended path may also be provided in accordance with example implementations of the present disclosure, the recommended path may include one or more key spots. The doctor may move the endoscope along the recommended path, to pass all key spots required by the endoscopic examination.

In accordance with example implementations of the present disclosure, the candidate motion track of the endoscope also may be directly generated based on the motion model 410A and the input data. It will be appreciated that the motion model 410A may be built in an end-to-end approach during the training. At this time, the input of the motion model 410A may be specified as an image sequence, and the output of the motion model 410A may be specified as the candidate motion track. Here, the candidate motion track may include a set of key spots corresponding to the input image sequence and a next candidate key spot. During use of the motion model 410A, a set of image sequences currently captured by the endoscope may be input into the motion model 410A, to obtain the candidate motion track. At this time, the doctor may operate the endoscope to move along the candidate motion track to traverse all key spots.

In accordance with example implementations of the present disclosure, the motion model 410A including an association between an image sequence and the candidate motion track may be directly obtained using historical sampled image sequences having labels and the historical sampled candidate motion tracks. Example implementations of the present disclosure may directly execute the training process based on the historical sampled data and obtain the corresponding model. In this way, the operation process is simplified and the efficiency for obtaining the candidate motion track is further improved.

In accordance with example implementations of the present disclosure, the information related to the operation behaviors of the endoscope may be transmitted and/or stored.

In accordance with example implementations of the present disclosure, information related to the current operation of the doctor may be output in real time and statistical and analytic functions are also provided, correspondingly. For example, the above described method 300 may further provide the following functions of: determining a duration of the endoscopic examination, determining information of the key spots that have been scanned, determining information of the key spots that have not been scanned, determining information of a next destination spot, determining the assessment for the endoscopic examination operations performed by the doctor, and determining whether the captured images related to various key spots are up to standard etc.

Figure 8:
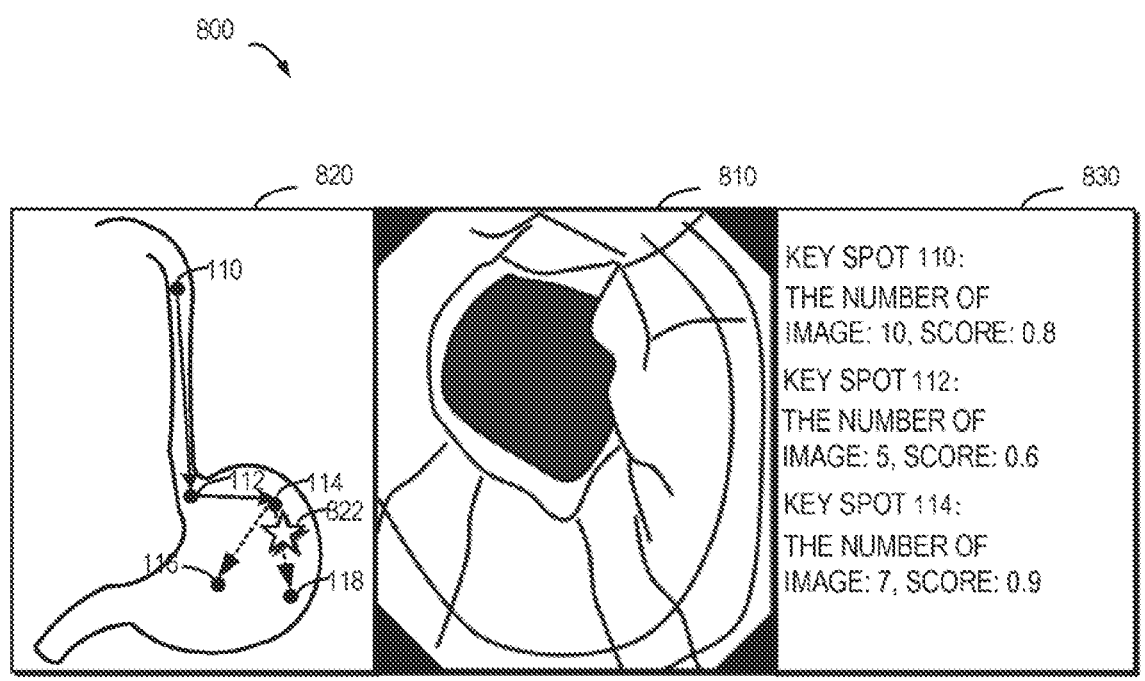
FIG. 8 schematically illustrates a block diagram of a user interface that provides a medical assistance operation in accordance with example implementations of the present disclosure.
Figure 9:
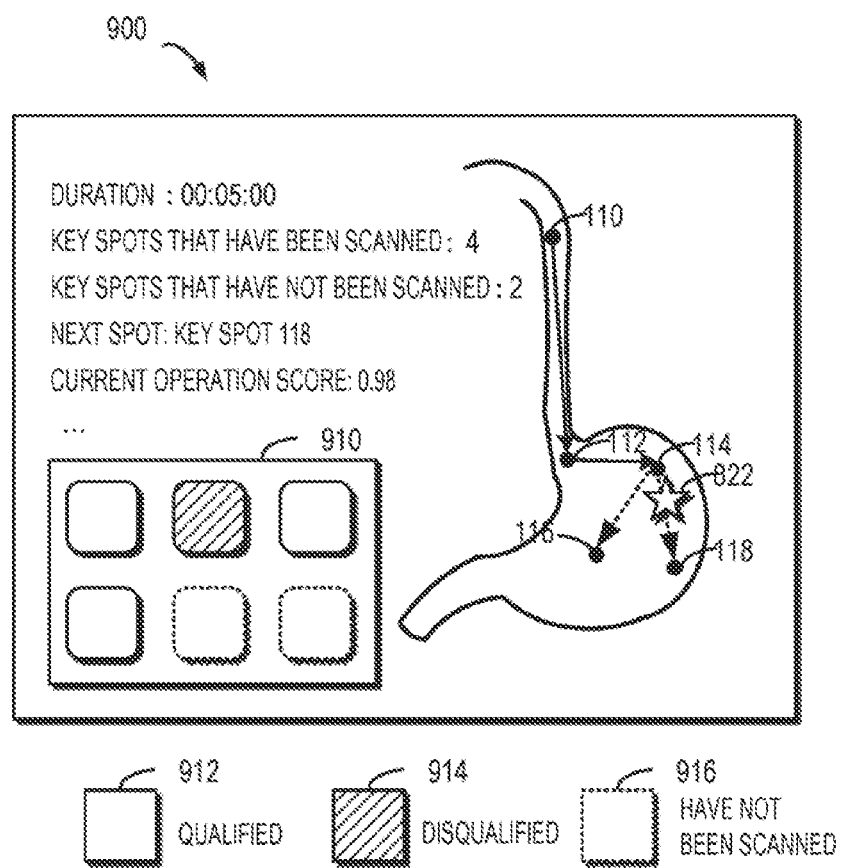
FIG. 9 schematically illustrates a block diagram of another user interface for providing a medical assistance operation in accordance with example implementations of the present disclosure.

In the following description, related functions related to outputting relevant information of the operation behaviors are described with reference to FIGS. 8 and 9. In accordance with example implementations of the present disclosure, the function of outputting the above information may be combined with the current display interface of the endoscope. FIG. 8 schematically illustrates a block diagram of a user interface 800 that provides a medical assistance operation in accordance with example implementations of the present disclosure. As shown, the user interface 800 may include: an image display unit 810 for displaying the video 220 captured by the endoscope 210 in real time; a motion track management unit 820 for displaying the motion track that has been passed by the endoscope 210 and an indication for the next destination spot; and a statistical information unit 830 for displaying information related to the images captured during the endoscopic examination.

As shown in the motion track management unit 820, the solid lines represent the motion track that has been covered by the endoscope 210: the key spot 110→the key spot 112→the key spot 114. The dotted lines denote a track from the current spot (i.e., the key spot 114) of the endoscope 210 to the next destination spot (i.e., key spots 116 and 118). According to the above method described with reference to FIG. 7B, the key spot 118 may be set as the next destination spot. Furthermore, a star label 822 may be used to indicate the key spot 118 as the recommended next destination spot. At this time, the doctor may move the endoscope 210 to the key spot 118 at the next time point.

As demonstrated in the statistical information unit 830, information related to the captured images may be displayed. For example, ten images have been selected for the key spot 110, and a comprehensive assessment for these ten images is 0.8. It is to be appreciated that an upper limit for the number of images expected to be captured for each key spot may be pre-defined. For example, the upper limit may be set to be 10. These ten images shown herein may be images of higher quality selected according to the method described above with reference to FIG. 6, and the assessment of 0.8 may be the comprehensive assessment obtained based on the assessment of respective image qualities.

In accordance with example implementations of the present disclosure, a lower limit may also be set for the image quality assessment. For example, it may be configured that only the images having an assessment of above 0.6 are selected. In accordance with example implementations of the present disclosure, the images expected to be stored may be selected in view of the upper limit of the number of images and the lower limit of the image quality assessment. The statistical information unit 830 further illustrates the statistical information related to other key spots. For the key spot 112, five images have been selected and the comprehensive assessment for the five images is 0.6. In terms of the key spot 114, seven images have been selected with a comprehensive assessment of 0.9.

In accordance with example implementations of the present disclosure, the user interface that manages the motion of the endoscope 210 may be separated from the current endoscope display interface. FIG. 9 schematically illustrates a block diagram of another user interface 900 for providing a medical assistance operation in accordance with example implementations of the present disclosure. As shown in FIG. 9, the information related to a medical assistance operation may be displayed in a separate user interface 900, in which the information related to the operation behaviors may be output.

In accordance with example implementations of the present disclosure, the information of the selected images of the key spots also may be displayed in an area 910. For example, the area 910 may include a thumbnail of the images. It is assumed that the endoscopic examination is required to capture images at six key spots, wherein the images at four key spots have been captured while the images at the rest two key spots have not been captured yet. In such a case, images for different types of the key spots may be represented by legend 912, 914 and 916 respectively. For example, the legend 912 indicates that a qualified image has been captured at a given key spot; the legend 914 denotes that a qualified image has yet not been captured at a given key spot; and the legend 916 indicates that a given key spot has not been scanned yet. Through the example implementations of the present disclosure, the key spots that have been scanned, the key spots that have not been scanned, and the key spots whose images are below the standard may be displayed to the doctor in a visible way, to facilitate the subsequent operations of the doctor.

In accordance with example implementations of the present disclosure, after selecting the images to be stored, an image abnormality associated with a given key spot may be identified based on the selected images. Moreover, the identified image abnormality may be displayed. Specifically, the image content may be analyzed by using image recognition techniques that are currently known and/or to be developed in the future, to determine possible image abnormality at the key spot. For example, the image abnormality may indicate ulcers or tumors, etc. In accordance with example implementations of the present disclosure, images that contain a possible abnormality may be identified to further assist the doctor to give a diagnosis.

In accordance with example implementations of the present disclosure, an operating state of the endoscope 210 is identified based on the input data. It is to be understood that the endoscope 210 may have various operating states during the operation. For example, when the endoscope 210 is initiated and inserted into the body of the patient, the image contents captured by the endoscope 210 may be different. Based on the analysis of the images captured by the endoscope 210, the patient being examined may be determined, or whether the endoscope is currently outside or inside the patient's body may be determined, or the part being examined may be determined (e.g., stomach or intestines etc.). For example, if a portion of the images in the image sequences relates to the outside of the body and a portion of the subsequent images changes to the inside of the body, it may be determined that the endoscope switches from outside to the inside of the body. Moreover, the switchover of the operating state may be identified.

For another example, between the examinations for two patients, patient switchover may be determined by analyzing the input data captured by the endoscope 210. Specifically, when the image sequences include images of an inside of the body, images of an outside of the body, and additional images of an inside of the body different from the previous examination, it may be determined that a switchover of patients occurs. For example, the endoscopic examination may involve different human body parts. At this time, the switchover of the examination spots may be determined by analyzing the images captured by the endoscope 210. To be specific, the switchover between the examination spots may be determined for endoscopes such as esophagoscope, gastroscope, duodenoscope, and colonoscopy, etc. By means of the example implementations of the present disclosure, the configuration related to a medical assistance operation may be selected in view of the detected switchover. For example, a corresponding motion model may be selected for the gastroscope and the colonoscopy.

It is to be understood that the endoscope 210 is required to be inserted into a patient's body during the endoscopic examination, and preparation work may be performed before the examination. In accordance with example implementations of the present disclosure, a preparation state of the person that is executing the endoscopic examination may be identified based on the input data. The preparation state herein describes whether the physical condition of the person is qualified for performing the endoscopic examination. The preparation work for the patient includes, for example, no eating or drinking, emptying the digestive tract, taking medicine according to the doctor's prescription to empty and cleanse the digestive tract etc. In addition, the preparation work for the doctor includes, for example, cleaning the stomach, blowing to the stomach to examine the rugae, etc.

Specifically, if the captured gastroscopic image includes food residue and the like, it may be determined that the patient is in a poor preparation state and fails to meet the requirements of emptying the digestive tract. If the captured gastroscopic image contains a large amount of secreta, it may be determined that the cleaning operation of the doctor is not thorough enough and the doctor may be indicated to carry out a further cleaning operation. Furthermore, the identified preparation level may be output via display or other indication ways. By means of the example implementations of the present disclosure, the patient and the doctor may be reminded respectively of the corresponding notices according to their preparation states.

It will be appreciated that although a specific example for determining the preparation state based on the images of the input data 230, the preparation state also may be determined according to a dedicated sensor (e.g., a sensor for monitoring in vivo environment parameters) disposed at the endoscope in accordance with example implementations of the present disclosure.

The endoscope 210, if moves fast inside the human body, may miss some key spots and further cause discomfort to the patient, such as nausea and pain, etc. As such, it is also expected to monitor the motion state of the endoscope 210 based on the stability of the motion, such that the motion track of the endoscope can cover all key spots and reduce the discomfort to the patient. In accordance with example implementations of the present disclosure, the stability of the motion of the endoscope 210 may be identified based on a set of time points when the endoscope 210 reaches a set of key spots, respectively. The stability here may represent a stable level of the motion of the endoscope 210 inside the patient's body. Furthermore, the identified stability may be displayed.

In accordance with example implementations of the present disclosure, a speed assessment for the moving speed of the endoscope 210 may be determined in view of the stability. For example, if the endoscope 210 moves for a relatively long distance within a short time, it means that the endoscope 210 moves a bit violently and this situation should be avoided. At this moment, a low speed assessment may be provided, which may remind the doctor that the endoscope moves a bit violently and the speed should be decreased to avoid missing certain key spots.

For another example, if the endoscope 210 moves at a moderate speed, a high speed assessment may be provided. For example, if the endoscope 210 only moves a relatively small distance within a long time period, the overall duration of the endoscopic examination will increase despite the smooth motion. In such a case, the speed assessment may also be reduced and the doctor is reminded to move the endoscope 210 to the next destination spot as fast as possible. For another example, the speed distribution during the endoscopic examination may also be monitored. Assuming that the endoscope 210 stays around five key spots for the first half of the examination and quickly goes by the rest thirty-three key spots in the second half, it is possible that the examination is not thorough enough in the second half round. A relatively low speed assessment may also be provided in such a case.

Compared to a technical solution in which the doctor's operation is determined to be thorough or not based on whether the overall examination time reaches an expected time period (e.g., 10 minutes), the example implementations of the present disclosure may determine whether the operation of the doctor is up to a predetermined standard according to the speed distribution of the endoscope 210. It will be appreciated that although a specific example of determining the stability based on the images of the input data 230 has been described above, the example implementations of the present disclosure also may determine the stability as a function of the speed sensor deployed at the endoscope.

Figure 10:
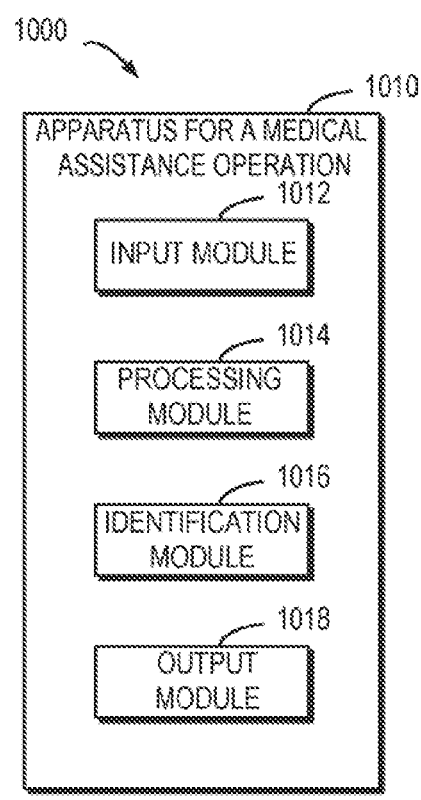
FIG. 10 schematically illustrates a block diagram of an apparatus for a medical assistance operation in accordance with example implementations of the present disclosure.

Details of the method for a medical assistance operation have been described above with reference to FIGS. 2-9. In the following description, various modules in the apparatus for a medical assistance operation are to be depicted with reference to FIG. 10, which schematically illustrates a block diagram of an apparatus 1010 for a medical assistance operation (or medical assistance information processing apparatus 1010) in accordance with example implementations of the present disclosure. As shown, there is provided an apparatus for a medical assistance operation 1010, which includes: an input module 1012 configured to obtain input data from an endoscope, and an output module 1018 configured to output information related to an operation behavior of the endoscope determined based on the input data.

In accordance with example implementations of the present disclosure, the input data includes image data captured at a plurality of spots during motion of the endoscope.

In accordance with example implementations of the present disclosure, the apparatus 1010 further comprises: a processing module 1014 configured to determine a next destination spot of the endoscope based on the input data.

In accordance with example implementations of the present disclosure, the processing module 1014 is further configured to: determine a motion track of the endoscope based on the input data.

In accordance with example implementations of the present disclosure, the motion track is presented by a set of predetermined key spots.

In accordance with example implementations of the present disclosure, the processing module 1014 is further configured to: determine a next destination spot of the endoscope based on the motion track.

In accordance with example implementations of the present disclosure, the processing module 1014 is further configured to: determine a set of candidate spots of the endoscope at a next time point; determine an assessment for respective candidate spots in the set of candidate spots; and selecting, based on the determined assessments, the next destination spot from the set of candidate spots.

In accordance with example implementations of the present disclosure, the processing module 1014 is further configured to: for a given candidate spot in the set of candidate spots, generate, based on the motion track and the given candidate spot, a candidate motion track of the endoscope; and determine, based on the motion track and a predetermined motion track of the endoscopic examination, the assessments of the candidate spots.

In accordance with example implementations of the present disclosure, the processing module 1014 is further configured to: determine an assessment of the motion track.

In accordance with example implementations of the present disclosure, the apparatus 1010 further comprises an identification module 1016 configured to: identify an operating state of the endoscope, and the operating state includes at least one of: patient identification, in vivo/in vitro, and examination spots.

In accordance with example implementations of the present disclosure, the identification module 1016 is further configured to: identify switchover of an operating state.

In accordance with example implementations of the present disclosure, the apparatus 1010 further comprises an identification module 1016 configured to: identify a preparation state of endoscopic examination spots based on the input data, wherein the preparation state indicates a qualification level of the examination spots for executing the endoscopic examination.

In accordance with example implementations of the present disclosure, the apparatus 1010 further comprises an identification module 1016 configured to: determine stability of the motion of the endoscope based on a set of time points when the endoscope arrives at the set of key spots, respectively.

In accordance with example implementations of the present disclosure, the processing module 1014 is further configured to: obtain the set of key spots based on the input data; and determine the motion track based on a time sequence of input data associated with the key spots.

In accordance with example implementations of the present disclosure, the processing module 1014 is further configured to: determine a set of image data in the input data that is mapped to the key spots; determining image quality assessments for the set of image data respectively based on image qualities of the set of image data; and selecting image data, from the set of image data, to be stored based on the determined image quality assessments.

In accordance with example implementations of the present disclosure, the apparatus 1010 further comprises an identification module 1016 configured to: identify an image abnormality at the key spots based on the selected image data.

In accordance with example implementations of the present disclosure, the processing module 1014 is further configured to: obtain a first model describing an endoscopic examination, wherein the first model includes an association between sampled input data captured at a plurality of sampled spots during execution of endoscopic examination and sampled motion tracks of an endoscope for capturing the sampled input data; and determining the motion track based on the first model and the input data.

In accordance with example implementations of the present disclosure, the processing module 1014 is further configured to: obtain the sampled input data captured according to a specification of endoscope operation during execution of endoscopic examination; obtaining the sampled motion tracks associated with the sampled input data; and training the first model based on the sampled input data and the sampled motion tracks.

In accordance with example implementations of the present disclosure, the processing module 1014 is further configured to: obtain a second model describing an endoscopic examination, wherein the second model includes an association between sampled input data captured at a plurality of sampled spots during execution of endoscopic examination and key spots corresponding to the plurality of spots where the sampled input data are captured; and determining a motion track of the endoscope based on the second model, the input data, and time when the image data is captured.

In accordance with example implementations of the present disclosure, determining information related to an operation behavior of the endoscope based on the input data includes determining at least one of the following: current spot of the endoscope; image data captured at the current spot; motion track of the endoscope; a next destination spot of the endoscope; statistical information of the input data; and statistical information of an operation behavior.

In accordance with example implementations of the present disclosure, the input data include at least one of: video data; a set of image sequences sorted according to time sequence; and image data having time information.

In accordance with example implementations of the present disclosure, the output module 1018 is further configured to: transmit information related to an operation behavior of the endoscope.

Figure 11:
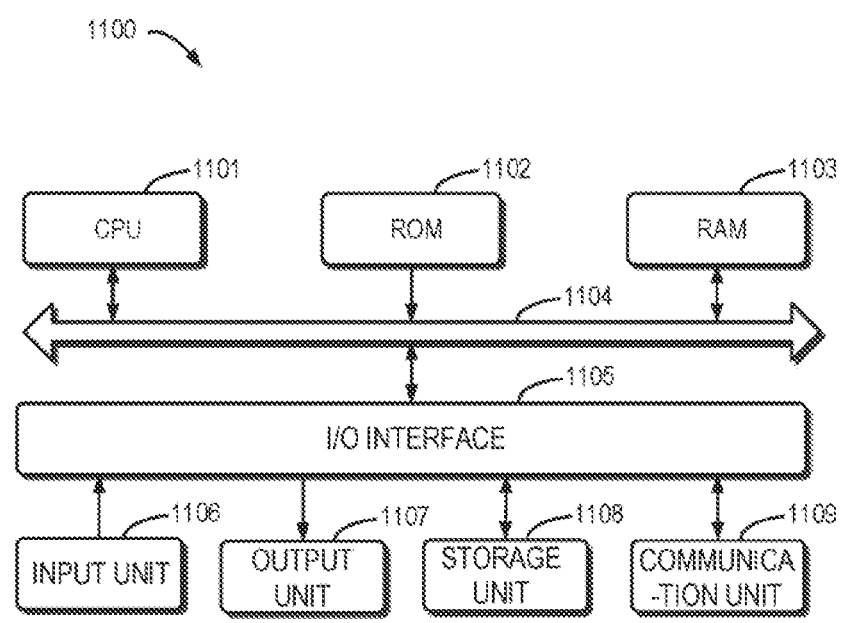
FIG. 11 schematically illustrates a schematic block diagram of a device for a medical assistance operation in accordance with example implementations of the present disclosure.

FIG. 11 illustrates a schematic block diagram of an example device 1100 for implementing example implementations of the present disclosure. For example, the computing device 130 shown in FIG. 1 may be implemented by the device 1100. As shown in FIG. 11, the device 1100 comprises a central process unit (CPU) 1101, which can execute various suitable actions and processing based on the computer program instructions stored in the read-only memory (ROM) 1102 or computer program instructions loaded in the random-access memory (RAM) 1103. The RAM 1103 can also store all kinds of programs and data required by the operation of the device 1000. CPU 1101, ROM 1102 and RAM 1103 are connected to each other via a bus 1104. The input/output (I/O) interface 1105 is also connected to the bus 1104.

A plurality of components in the device 1000 is connected to the I/O interface 1105, including: an input unit 1106, such as keyboard, mouse and the like; an output unit 1107, e.g., various kinds of display and loudspeakers etc.; a storage unit 1108, such as magnetic disk and optical disk etc.; and a communication unit 1109, such as network card, modem, wireless transceiver and the like. The communication unit 1109 allows the device 1100 to exchange information/data with other devices via the computer network, such as Internet, and/or various telecommunication networks.

The above described procedure and processing, such as method 300, may be executed by the processing unit 1101. For example, in some implementations, the method 300 can be implemented as a computer software program tangibly included in the machine-readable medium, e.g., storage unit 1108. In some example implementations, the computer program can be partially or fully loaded and/or mounted to the device 1100 via ROM 1102 and/or communication unit

1109. When the computer program is loaded to RAM 1103 and executed by the CPU 1101, one or more steps of the above described method 300 can be implemented.

In accordance with example implementations of the present disclosure, there is provided a device for a medical assistance operation, including: at least one processing unit; at least one memory coupled to the at least one processing unit and storing instructions to be executed by the at least one processing unit, the instructions, when executed by the at least one processing unit, causing the device to perform the above described method 300.

The present disclosure can be method, apparatus, system, and/or computer program product. The computer program product can include a computer-readable storage medium, on which the computer-readable program instructions for executing various aspects of the present disclosure are loaded.

The computer-readable storage medium can be a tangible apparatus that maintains and stores instructions utilized by the instruction executing apparatuses. The computer-readable storage medium can be, but not limited to, such as electrical storage device, magnetic storage device, optical storage device, electromagnetic storage device, semiconductor storage device or any appropriate combinations of the above. More concrete examples of the computer-readable storage medium (non-exhaustive list) include: portable computer disk, hard disk, random-access memory (RAM), read-only memory (ROM), erasable programmable read-only memory (EPROM or flash), static random-access memory (SRAM), portable compact disk read-only memory (CD-ROM), digital versatile disk (DVD), memory stick, floppy disk, mechanical coding devices, punched card stored with instructions thereon, or a projection in a slot, and any appropriate combinations of the above. The computer-readable storage medium utilized here is not interpreted as transient signals per se, such as radio waves or freely propagated electromagnetic waves, electromagnetic waves propagated via waveguide or other transmission media (such as optical pulses via fiber-optic cables), or electric signals propagated via electric wires.

The described computer-readable program instruction can be downloaded from the computer-readable storage medium to each computing/processing device, or to an external computer or external storage via Internet, local area network, wide area network and/or wireless network. The network can comprise copper-transmitted cable, optical fiber transmission, wireless transmission, router, firewall, switch, network gate computer and/or edge server. The network adapter card or network interface in each computing/processing device receives computer-readable program instructions from the network and forwards the computer-readable program instructions for storage in the computer-readable storage medium of each computing/processing device.

The computer program instructions for executing operations of the present disclosure can be assembly instructions, instructions of instruction set architecture (ISA), machine instructions, machine-related instructions, microcode, firmware instructions, state setting data, or source codes or target codes written in any combinations of one or more programming languages, wherein the programming languages comprise object-oriented programming languages, e.g., Smalltalk, C++ and so on, and traditional procedural programming languages, such as "C" language or similar programming languages. The computer-readable program instructions can be implemented fully on the user computer, partially on the user computer, as an independent software package, partially on the user computer and partially on the remote computer, or completely on the remote computer or server. In the case where remote computer is involved, the remote computer can be connected to the user computer via any type of networks, including local area network (LAN) and wide area network (WAN), or to the external computer (e.g., connected via Internet using the Internet service provider). In some example implementations, state information of the computer-readable program instructions is used to customize an electronic circuit, e.g., programmable logic circuit, field programmable gate array (FPGA) or programmable logic array (PLA). The electronic circuit can execute computer-readable program instructions to implement various aspects of the present disclosure.

Various aspects of the present disclosure are described here with reference to flow chart and/or block diagram of method, apparatus (system) and computer program products according to example implementations of the present disclosure. It should be understood that each block of the flow chart and/or block diagram and the combination of various blocks in the flow chart and/or block diagram can be implemented by computer-readable program instructions.

The computer-readable program instructions can be provided to the processing unit of general-purpose computer, dedicated computer or other programmable data processing apparatuses to manufacture a machine, such that the instructions that, when executed by the processing unit of the computer or other programmable data processing apparatuses, generate an apparatus for implementing functions/actions stipulated in one or more blocks in the flow chart and/or block diagram. The computer-readable program instructions can also be stored in the computer-readable storage medium and cause the computer, programmable data processing apparatus and/or other devices to work in a particular manner, such that the computer-readable medium stored with instructions comprises an article of manufacture, including instructions for implementing various aspects of the functions/actions stipulated in one or more blocks of the flow chart and/or block diagram.

The computer-readable program instructions can also be loaded into computer, other programmable data processing apparatuses or other devices, so as to execute a series of operation steps on the computer, other programmable data processing apparatuses or other devices to generate a computer-implemented procedure. Therefore, the instructions executed on the computer, other programmable data processing apparatuses or other devices implement functions/actions stipulated in one or more blocks of the flow chart and/or block diagram.

The flow chart and block diagram in the drawings illustrate system architecture, functions and operations that may be implemented by system, method and computer program product according to multiple implementations of the present disclosure. In this regard, each block in the flow chart or block diagram can represent a module, a part of program segment or code, wherein the module and the part of program segment or code include one or more executable instructions for performing stipulated logic functions. In some alternative implementations, it should be noted that the functions indicated in the block can also take place in an order different from the one indicated in the drawings. For example, two successive blocks can be in fact executed in parallel or sometimes in a reverse order dependent on the involved functions. It should also be noted that each block in the block diagram and/or flow chart and combinations of the blocks in the block diagram and/or flow chart can be implemented by a hardware-based system exclusive for executing stipulated functions or actions, or by a combination of dedicated hardware and computer instructions.

Various implementations of the present disclosure have been described above and the above description is only exemplary rather than exhaustive and is not limited to the implementations of the present disclosure. Many modifications and alterations, without deviating from the scope and spirit of the explained various implementations, are obvious for those skilled in the art. The selection of terms in the text aims to best explain principles and actual applications of each implementation and technical improvements made in the market by each implementation, or enable those ordinary skilled in the art to understand implementations of the present disclosure.

We claim:

1. A device for a medical assistance operation, comprising:
   at least one processor configured to:
      obtain input data from an endoscope;
      obtain a first model describing an endoscopic examination, wherein the first model comprises an association between sampled input data captured at a plurality of sampled spots during execution of the endoscopic examination and a predetermined motion track of an endoscope for capturing the sampled input data; and
      determine information related to an operation behavior of the endoscope based on the first model and the input data, wherein the information comprises a motion track, wherein the motion track is a motion track during the endoscopic examination; and
      cause display of an indication in real time of a next key spot to which a doctor is to guide the endoscope, wherein the information comprises the next key spot.

2. The device of claim 1, wherein the input data comprises image data captured at a plurality of sites during motion of the endoscope.

3. The device of claim 1, wherein the processor is further configured to:
   determine a next destination site of the endoscope based on the input data.

4. The device of claim 3, wherein the processor is further configured to:
   determine a set of candidate sites for a next time point for the endoscope;
   determine assessments for candidate sites in the set of candidate sites, respectively; and
   select, based on the determined assessments, the next destination site from the set of candidate sites.

5. The device of claim 1, wherein the processor is further configured to:
   obtain a set of key sites based on the input data; and the motion track based on a time sequence of input data associated with the key sites.

6. The device of claim 1, wherein the processor is further configured to determine the motion track of the endoscope based on the input data by:
   obtaining a second model describing an endoscopic examination, wherein the second model comprises an association between sampled input data captured at a plurality of sampled spots during execution of an endoscopic examination and a plurality of key spots corresponding to the plurality of spots where the sampled input data are captured;
   determining the motion track of the endoscope based on the second model, the input data and the time when the image data is captured; and
   cause display of a second indication, wherein the second indication is a current operation score in real time, wherein the current operation score is a degree of match between the motion track during the endoscopic examination and the predetermined motion track, wherein the predetermined motion track is a sequence of a series of key spots defined by a specification for operating the endoscope.

7. The device of claim 1, wherein the device is further configured to:
   determine that the endoscope is at a first key spot at a first time,
   determine an operation score of the motion track during the endoscopic examination according to a sequence of directions the endoscope has recently moved in in order to reach the first key spot,
   wherein the operation score measures a match between the motion track and the predetermined motion track, wherein the predetermined motion track is a sequence of key spots defined by a specification for operating the endoscope, and
   provide the operation score to the doctor via a display, wherein the operation score is configured to assist the doctor in real time in manipulating the endoscope inside a human body.

* * * * *